United States Patent
Mooreville (10) Patent No.: US 10,500,379 B2
(45) Date of Patent: Dec. 10, 2019

(54) URETHROTOME-DILATOR

(71) Applicant: Michael Mooreville, Landsowne, PA (US)

(72) Inventor: Michael Mooreville, Landsowne, PA (US)

( * ) Notice: Subject to any disclaimer, the term of this patent is extended or adjusted under 35 U.S.C. 154(b) by 433 days.

(21) Appl. No.: 15/089,158

(22) Filed: Apr. 1, 2016

(65) Prior Publication Data

US 2017/0281917 A1  Oct. 5, 2017

(51) Int. Cl.
| | | |
|---|---|---|
| A61M 29/00 | (2006.01) | |
| A61B 17/32 | (2006.01) | |
| A61B 34/00 | (2016.01) | |
| A61M 25/09 | (2006.01) | |
| A61B 90/00 | (2016.01) | |
| A61B 17/00 | (2006.01) | |

(52) U.S. Cl.
CPC ..... A61M 29/00 (2013.01); A61B 17/320016 (2013.01); A61B 34/76 (2016.02); A61M 25/09 (2013.01); A61B 2017/00526 (2013.01); A61B 2017/00867 (2013.01); A61B 2090/062 (2016.02); A61M 2210/1089 (2013.01)

(58) Field of Classification Search
CPC ................. A61M 29/00; A61M 25/09; A61M 2210/1089; A61B 34/76; A61B 17/320016; A61B 2090/062; A61B 2017/00526; A61B 2017/00867; A61B 2017/320044; A61B 2017/320052

See application file for complete search history.

(56) References Cited

U.S. PATENT DOCUMENTS

| | | | | |
|---|---|---|---|---|
| 4,582,066 | A | * | 4/1986 | Barnes .................. A61B 8/065 600/459 |
| 5,697,944 | A | * | 12/1997 | Lary .............. A61B 17/320725 604/22 |
| 5,817,061 | A | | 10/1998 | Goodwin et al. |
| 5,817,127 | A | | 10/1998 | Borodulin et al. |
| 5,899,916 | A | * | 5/1999 | Casparian .......... A61B 17/3468 606/187 |
| 5,968,067 | A | | 10/1999 | Mooreville et al. |

(Continued)

OTHER PUBLICATIONS

International Search Report and Written Opinion, PCT/US2010/025210, dated Jun. 9, 2017.

*Primary Examiner* — Jing Rui Ou
(74) *Attorney, Agent, or Firm* — Noah Lerman; Bryan, Cave, Leighton Paisner LLP (57) ABSTRACT

Urethrotome dilators for dilating a urethral stricture, and methods for forming and using the same are disclosed. In some embodiments, the urethrotome dilator includes a first distal end with a dilating head, a second proximal end with a handle, and a stem for connecting the first end to the second end. The dilating head may have a first region, a second region, and a channel for receiving a guidewire. The first region of the dilating head may have a substantially conical surface, with a vertex at its distal end and a base at its proximal end. The second region may have a substantially flat surface and a blade for stretching tissue. The blade may be integrally formed within the second region and may extend from the flat surface. The top edge of the blade may be tapered and blunt, while the two opposing sides of the blade may be formed with sharp corners for cutting tissue.

29 Claims, 9 Drawing Sheets

(56) References Cited

U.S. PATENT DOCUMENTS

| | | | |
|---|---|---|---|
| 2001/0012946 A1* | 8/2001 | MacKenzie | A61B 17/3415 606/185 |
| 2002/0032447 A1* | 3/2002 | Weikel | A61B 17/1671 606/86 R |
| 2002/0035373 A1* | 3/2002 | Carlson | A61B 17/3415 606/185 |
| 2003/0074007 A1* | 4/2003 | Rosengart | A61B 17/11 606/108 |
| 2006/0004398 A1* | 1/2006 | Binder, Jr. | A61B 17/3417 606/191 |
| 2007/0198045 A1* | 8/2007 | Morton | A61B 17/3439 606/191 |
| 2007/0208366 A1* | 9/2007 | Pellegrino | A61M 29/02 606/198 |
| 2009/0018565 A1* | 1/2009 | To | A61B 17/320758 606/159 |
| 2009/0125030 A1* | 5/2009 | Tebbe | A61B 17/3421 606/90 |
| 2009/0281564 A1* | 11/2009 | Kontos | A61M 25/104 606/194 |
| 2011/0087234 A1 | 4/2011 | Ayala et al. | |
| 2016/0158501 A1 | 6/2016 | Farris | |
| 2016/0287284 A1* | 10/2016 | Smith | A61B 17/320725 |

\* cited by examiner

URETHROTOME-DILATOR

FIELD OF THE INVENTION

The present invention pertains to surgical instruments in the field of urology used in the treatment of urethral strictures. In particular, the present invention relates to surgical instruments that provide dilating functions with functions of a non-mechanical urethrotome that can be passed over a guidewire for improved localization and control.

BACKGROUND OF THE INVENTION

Urethral strictures are a common problem in the practice of urology. Some of the strictures are considered "soft" and respond easily to dilation with sounds or bougies as noted in the text "Campbell's Urology", $8^{th}$ edition, page 3919. The procedure involves the passage of serially increasing size rods to the desired diameter. Other strictures are categorized as "hard" and are more resistant to plain dilation, requiring actual cutting of hard fibrous bands transurethrally.

Current optical or nonvisual urethrotomes allow for the cutting of these difficult strictures under anesthesia. The ultimate goal is for the larger lumen of the urethra to heal in the open position. One such device described by W. E. Washburn, U.S. Pat. No. 762,366, has a sheath containing a mechanical dilating head and a retractable blade, which can be used to cut the scar within the urethra in a blind fashion. There are other urethrortome-dilator combinations, which can stretch as well as cut the scar, like the Otis Urethrotome (V. Mueller Catalog). This is a mechanical device with a knob controlling the expandable portion of the instrument and a channel guide for insertion of a sharp blade, which can slide in its track and cut scar tissue in a blind fashion.

One significant disadvantage to these instruments are their "blind nature", which can lead to complications like bleeding as well as more infrequent injuries, when the cuts are deeper than intended, and can affect erectile function and possibly incontinence if the sphincter area is traumatized. A direct vision urethrotome was developed by Sachse to allow cutting of strictures under vision (J R Soc Med 1978 August; 71(8) 596-599). The Sachse urethrotome allows for better control of the depth and extent of the incision of the cutting blade by visual observation. The instrument has a sheath, which allows for an endoscopic viewing lens, a light source, as well as a working element, which controls the blade.

However, the surgical instruments described above are typically made from multiple components, and mechanical interlocking gears or junctions. For example, blade-equipped urethrotomes for cutting tissue typically use gears and junctions to enable a medical professional to pull a trigger that exposes the blade when he or she attempts to cut tissue. Because of the numerous components typically needed to provide both cutting and stretching functionality to a urethrotome, such instruments are typically cumbersome to use and maintain. Further, urethrotomes are not typically built with an integrally formed exposed blade because of the risk of unintentionally cutting or damaging tissue.

Accordingly, what is needed are systems and methods for providing a urethrotome capable of both dilating and cutting urethral tissue, and that is inexpensive and simple to maintain.

SUMMARY OF THE INVENTION

In various embodiments, the invention provides methods, systems and apparatuses for providing a urethrotome dilator for dilating a urethral stricture. The urethrotome dilator may include a first distal end with a dilating head, a second proximal end with a handle, and stem that joins the two together. The dilating head may have a first region, a second region, and a channel running in the longitudinal axis in the center of the dilating head for receiving a guidewire. The first region of the dilating head may have a substantially conical surface, with a vertex at its distal end and a base at its proximal end. The second region may have a substantially flat surface and a blade for stretching or cutting tissue. The handle at the second proximal end may be used to control the movement and orientation of the first distal end.

The blade may be integrally formed within the second region and may extend from the flat surface of the dilating head. The blade may have a distal blade end, a proximal blade end, a top edge, and two opposing sides. The top edge of the blade may be tapered and blunt, while the two opposing sides of the blade may be formed with substantially sharp corners for cutting tissue. Because the top edge of the blade is blunt, it may come into contact with normal tissue without causing damage. The top edge of the blade lifts and stretches tissue within a stricture exposing fibrous bands to the cutting lateral edges. While the blunt top edge of the blade may be used to push or move tissue, the substantially sharp corners formed by opposing sides of the blade may be used to cut or sever tissue. In this way, the dilating head may be used to selectively move or cut tissue as it advances to or through a stricture.

The stem is configured to be flexible and to transmit resistance produced at the dilating head to the handle as haptic feedback. When the dilating head encounters tissue or an obstruction that would cause resistance as the urethrotome is advanced through the urethra, the resistance is felt at the handle as haptic feedback. In this way, the urethrotome dilator can be used without any visual aid, such as for example, a scope, enabling a medical professional to advance the urethrotome dilator to or through a stricture by relying on the tactile feedback of the instrument. If the stem is bent as it advances to or through a stricture it is additionally configured to return to its original configuration.

A medical professional may use the urehtrotome dilator to dilate a urethral stricture by advancing the dilating head to or through the stricture. As it advances, the tapered blade dilates the urethral stricture. If the dilating head encounters an obstruction or scar tissue, haptic feedback will be transmitted from the dilating head through the stem to the handle. A medical professional may control the movement and orientation of the urethrotome dilator based on the haptic feedback to cut, stretch, or move the obstruction or scar tissue with the blade's blunt edge or sharp corners.

One object of invention, is to provide a cutting-dilator that is substantially simpler and easier to operate than common urethortomes, and is constructed without moving parts. Another object of the invention is to improve the control of the urethrotome dilator by guiding it over a guide-wire. Instead of guiding the urethrotome dilator using an optical aid, the blunt part of the dilator easily pushing aside normal, flexible tissue, while the cornered sharp edges selectively engaging fibrous bands within a stricture.

DETAILED DESCRIPTION OF THE INVENTION

Figure 1:
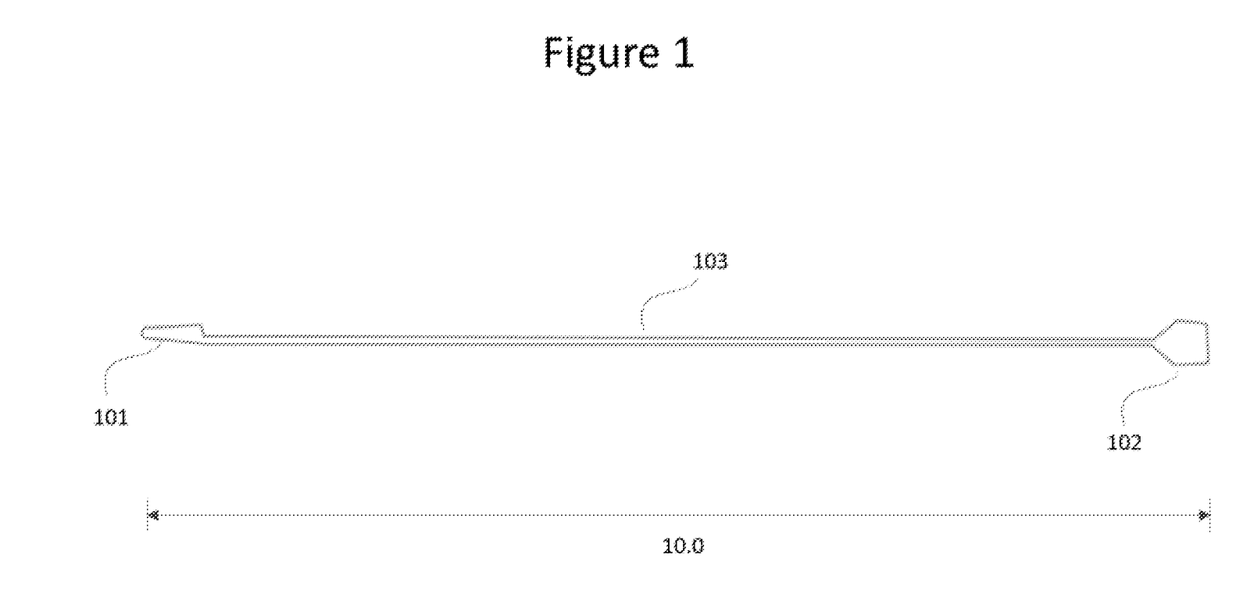
FIG. 1 is a urethrotome dilator according to some embodiments of the invention.

A urethrotome dilator according to some embodiments of the invention is shown in FIG. 1. The urethrotome dilator comprises a first end 101, a second end 102 having a handle for manipulating the urethrotome dilator, and a stem 103 that couples the first end to the second end. The first end is distal (i.e., furthest away from the medical professional operating the instrument, and the end that first enters into a patient), and has a dilating head for dilating a urethral stricture. The second end is a proximal end that is opposite of the first end, having a handle for controlling the movement and orientation of the dilator urethrotome.

In one aspect of the invention, the stem 103 is configured to transmit resistance produced at the dilating head to the handle as haptic feedback. As explained above, the stem is coupled to the dilating head through a recess. Friction or resistance encountered by the dilating head is thus transmitted to the stem via the recess. The haptic feedback indicates a level of resistance encountered by the dilating head. Thus, if the dilating head encounters tissue or an obstruction that would cause resistance as the urethrotome is advanced through the urethra, the resistance may be felt at the handle. In this way, a medical professional may advance the urethrotome to or through a stricture without the use of a scope or similar visual aid, and instead rely on the tactile feedback of the instrument.

In another aspect of the invention, the stem is constructed of a material that enables the stem to flexibly bend in response to pressure at the handle and the urethral stricture. As the stem is advanced through the urethra, the non-linear deflections in the shape of the stricture may cause pressure to be imparted at various points along the stem. Whereas a rigid or inflexible stem would dig or prod into the stricture causing pain, discomfort, or a false passage, the material of the stem gives in response to the pressure. The material may include surgical steel, biocompatible plastic, nitinol, and similar materials.

Figure 2A:
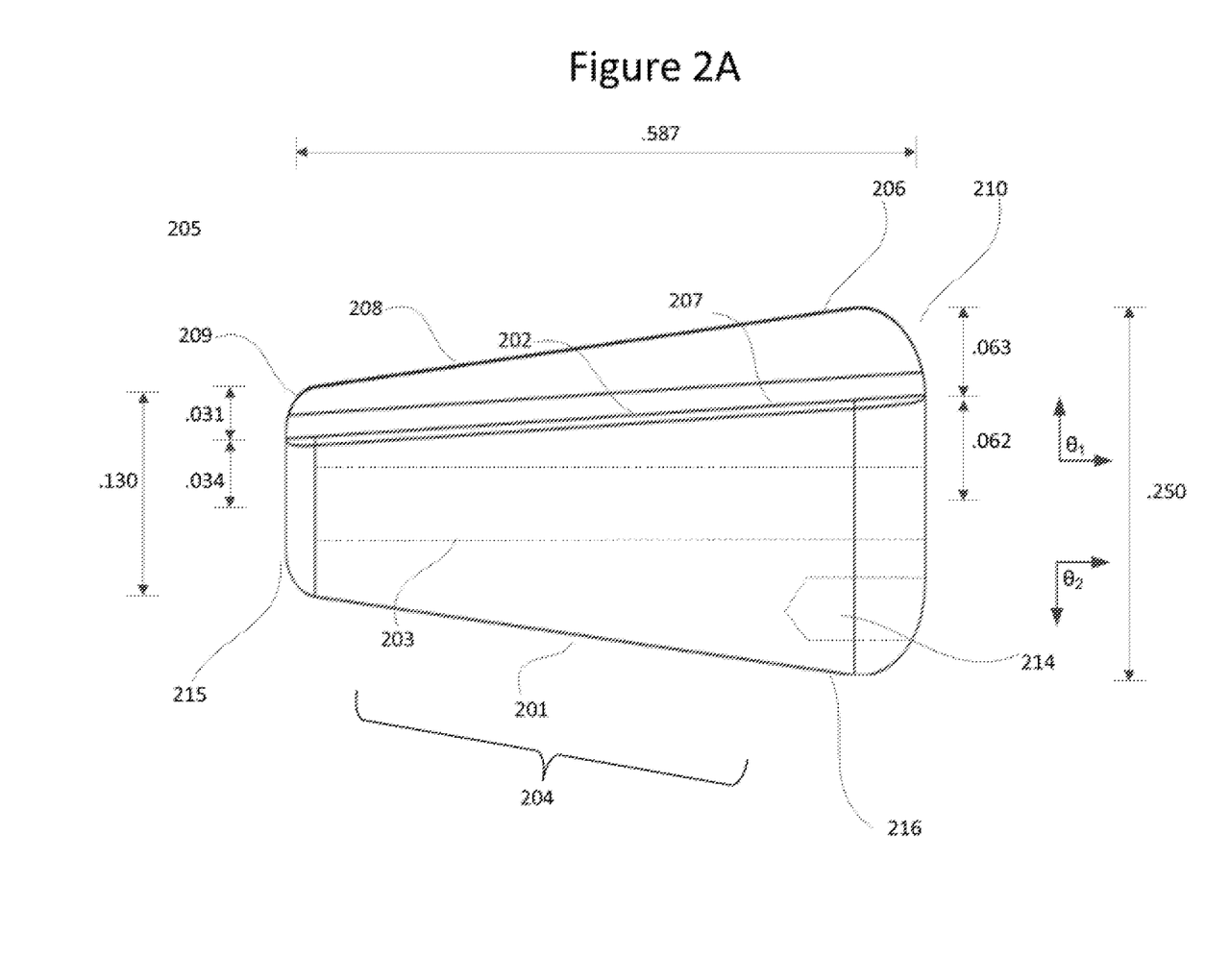
FIGS. 2A, 2B, 2C and 2D are cross-sectional and perspective views of a dilator-urethrotome according to embodiments of the invention.

A side cross-sectional view of a dilating head of the first distal end according to some embodiments of the invention is shown in FIG. 2A. The dilating head may be formed with a first region 201, a second region 202, and a channel 203. The first region 201 may have a substantially conical surface 204, with the vertex of the cone located at the distal end of the dilating head 205 and the base of the cone located at the proximal end of the dilating head 206. The first region 201 may be formed with a recess 214 to receive a stem, as described in more detail below. The second region 202 may have a substantially flat surface 207 and a blade 208. As described in more detail below, blade 208 may be used to stretch the tissue lining the urethral stricture. In a preferred embodiment, the base of cone located at the proximal end of the dilating head 206 may have a radius of 0.125 in, and a conical configuration ranging from 8 to 18 F. (One unit of diameter is equal to 3 F).

According to some embodiments of the invention, blade 208 is integrally formed within the second region 202. As explained in more detail below, blade 208 is integrally formed within the second region 202 through a casting process whereby the first region 201 of the dilating head and the blade 208 are formed from a single mold. The blade 208 may have a distal blade end 209, a proximal blade end 210, a top edge 211, and two opposing sides 212 and 213.

In one aspect of the invention, the top edge of the blade 211 may come into contact with fibrous tissue without causing damage. As described below, the top edge of the blade 211 is formed with a substantially flat and wide surface creating a blunt edge. In this way, the top edge of the blade 211 may be used to move or stretch tissue in a stricture. For example, the top edge of the blade 211 may be used to lift or push tissue within the stricture.

In another aspect of the invention, the corners formed on the top edge of the blade may be used to cut or sever tissue. As described in more detail below, the top edge of the blade 211 and the two opposing sides 212 and 213 are formed to create substantially sharp corners. For example, the top edge of the blade 211 and the two opposing sides 212 and 213 may form a 90° angle. Thus, while the blunt top edge of the blade 211 may be used to push or move tissue, the sharp corners formed by opposing sides 212 and 213 may be used to cut or sever tissue. For example, if the urethrotome encounters a blockage or obstruction formed by tissue, the sharp corners formed by the top edge of the blade 211 and two opposing sides 212 and 213 may be used to cut or sever the tissue. The blunt top edge of the blade 211 may be used to push or move the cut tissue, allowing the urethrotome to advance to or cut through the stricture. In this way, the dilating head may be used to selectively move or cut tissue as it advances to or through a stricture.

In some embodiments of the invention, the height of the blade is tapered from the proximal blade end 210 to the distal blade end 209. The tapering is created by forming the proximal blade end 210 with a height greater than the distal blade end 209. For example, the height of the distal blade end of the dilating head from the flat surface may range from 0.015 in. to 0.031 in. and the height of the proximal blade end of the dilating head from the flat surface may range from 0.048 in. to 0.063 in. As shown in FIG. 2, the blade with tapered height may have a top blade edge 211 formed at an angle with respect to a flat horizontal axis. In a preferred embodiment of the invention, the angle of the tapering $\theta_1$ is between 2° and 7°. In two preferred embodiments, angles $\theta_1$ are approximately 2.71° or 6.7°. The gradual incline of the tapered blade allows the distal end to incrementally stretch and dilate fibrous tissues as it advances in the urethra. As described above, the top edge of the blade 211 is substantially blunt thereby allowing it to stretch, dilate and cut fibrous tissue within the stricture without cutting or damaging normal tissues.

Similarly, the conical surface of the dilating head may be angled with respect to the channel to allow the first end to incrementally stretch and dilate fibrous tissues as it advances in the urethra. In some embodiments of the invention, the angle of the conical surface of the dilating head with respect to channel $\theta_2$ is approximately between 4° and 9°. In three preferred embodiments, angles $\theta_2$ are approximately 4.21°, 5.80°, or 8.42°.

In some embodiments of the invention, the first region and second region have a distal end that forms a tip of the dilating head, the tip having a curved edge 215 for dilating the urethral stricture while advancing the urethrotome. In a preferred embodiment, the tip has a radius of curvature of 0.03 in. Similarly, in some embodiments of the invention, the first region and second region have a proximal end that form a rear of the dilating head 216, the rear having a curved edge for dilating the urethral stricture while removing the urethrotome. In a preferred embodiment, the rear has a radius of curvature of 0.06 in.

In some embodiments of the invention, a channel 203 is formed longitudinally through the dilating head to guide the urethrotome through a stricture with a guidewire. As described in more detail below, the channel 203 may be formed by drilling or boring a hole through a solid molded cast of the dilating head. The channel 203 is formed with a diameter large enough to pass a guide-wire that guides the insertion of the urethrotome through the urethra. In this way, a guidewire may be passed through the channel 203, and used to guide the urethrotome as it advances to or through the stricture. In a preferred embodiment, the channel 203 has a radius of 0.047 in., and the recess 214 has a radius of 0.0492 in. In some embodiments of the invention, channel 203 is positioned at the geometric center of the dilating head, leaving room for a blade and stem recess to be formed on the top and lower portions of the dilating head.

Figure 2B:
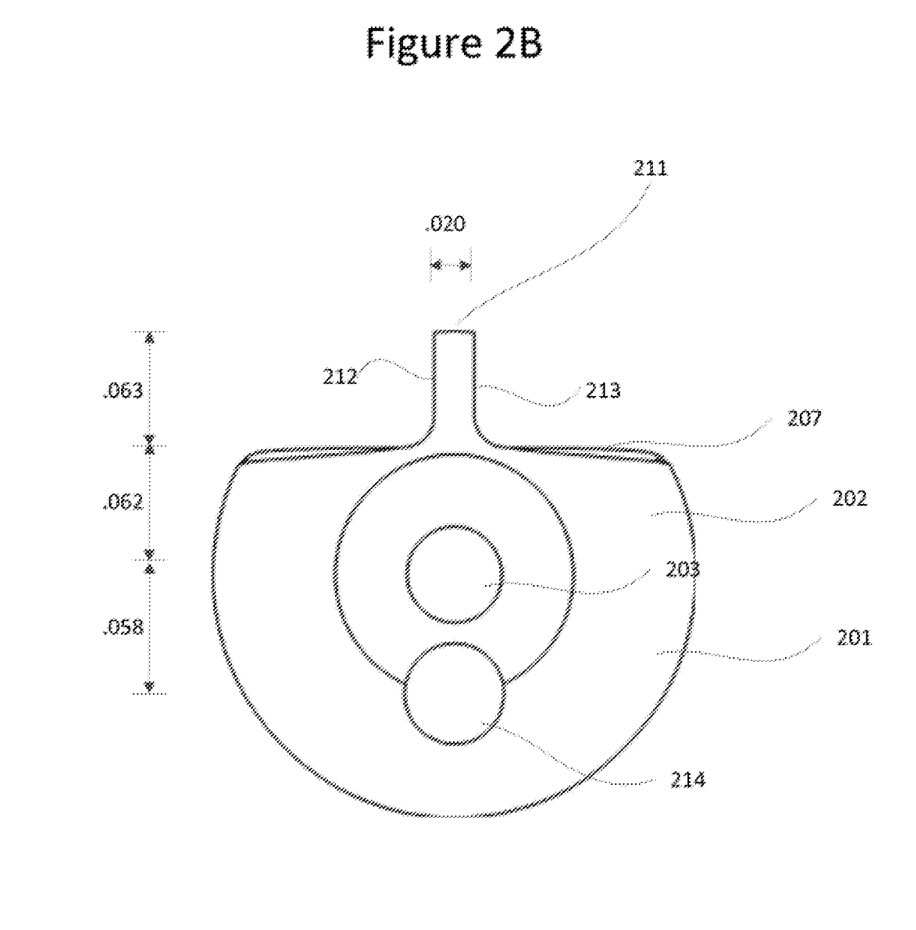
Figure 2C:
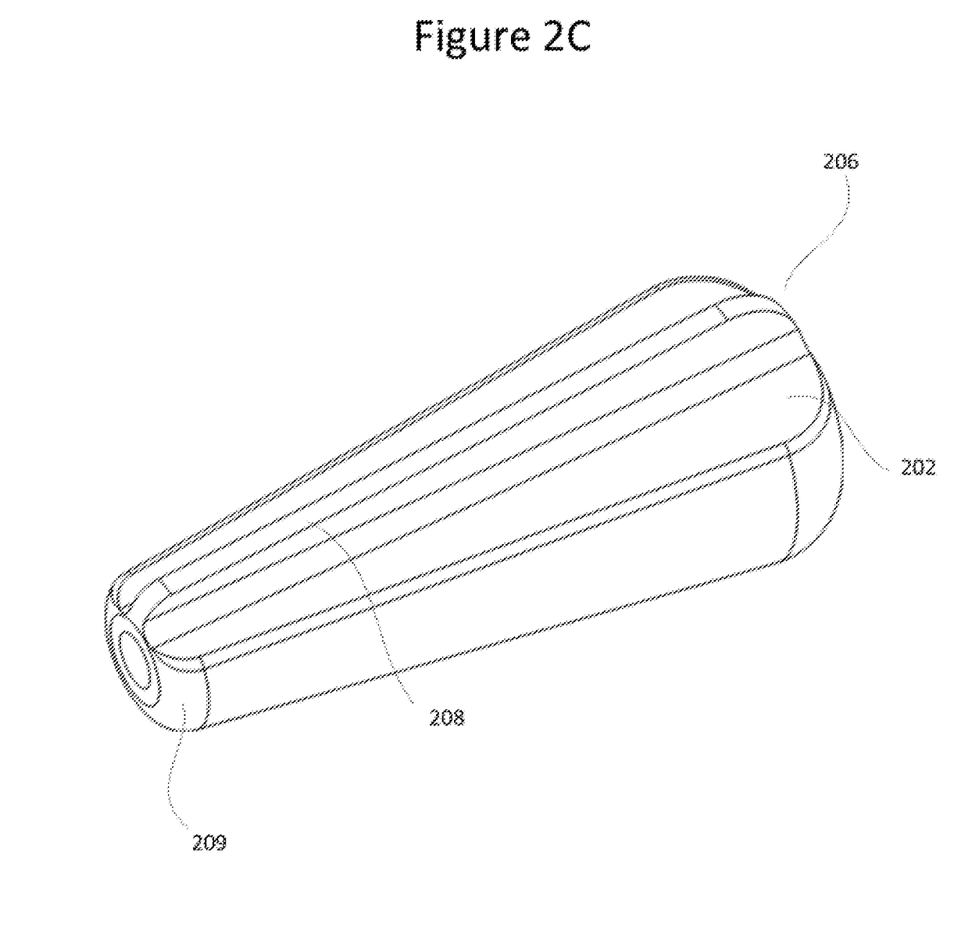
Figure 2D:
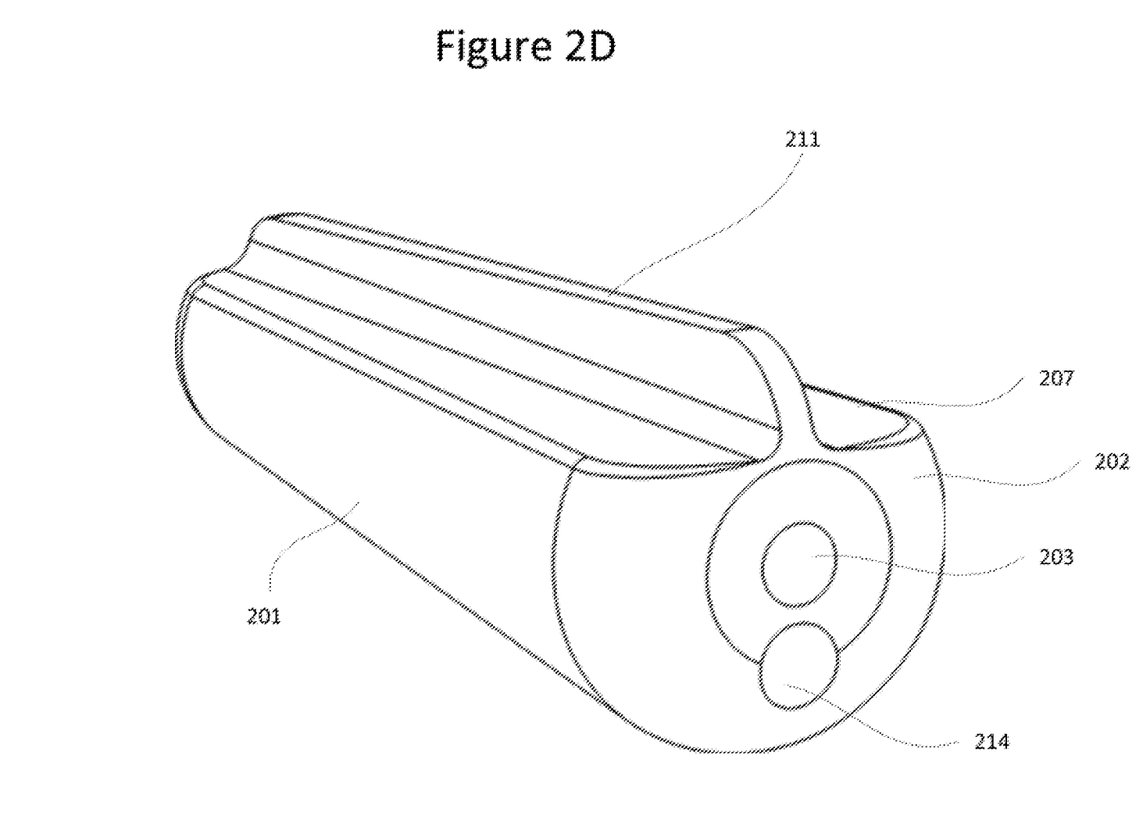

A cross-sectional view of the rear of the dilating head according to some embodiments of the invention is shown in FIG. 2B. FIGS. 2C and 2D show front and rear perspective views of the dilating head according to some embodiments of the invention. As these Figures show, channel 203 may be positioned in the geometric center of the dilating head allowing room for a recess 214 and blade 208 to be formed in the first and second region. For example, the first region 201 may have a recess 214 to receive and affix a stem positioned below the channel 203. In some embodiments, the stem may be affixed to the recess 214 with an adhesive or bonding material. In other embodiments, the recess 214 may include spiral grooves that fasten the stem to the dilating head. The second region 202 may have a substantially flat surface 207 and a blade 208. The flat surface 207 allows the blade 208 to be formed with two opposing sides 212 and 213 that are used to create the sharp corners for cutting and severing tissues as described above.

Figure 3A:
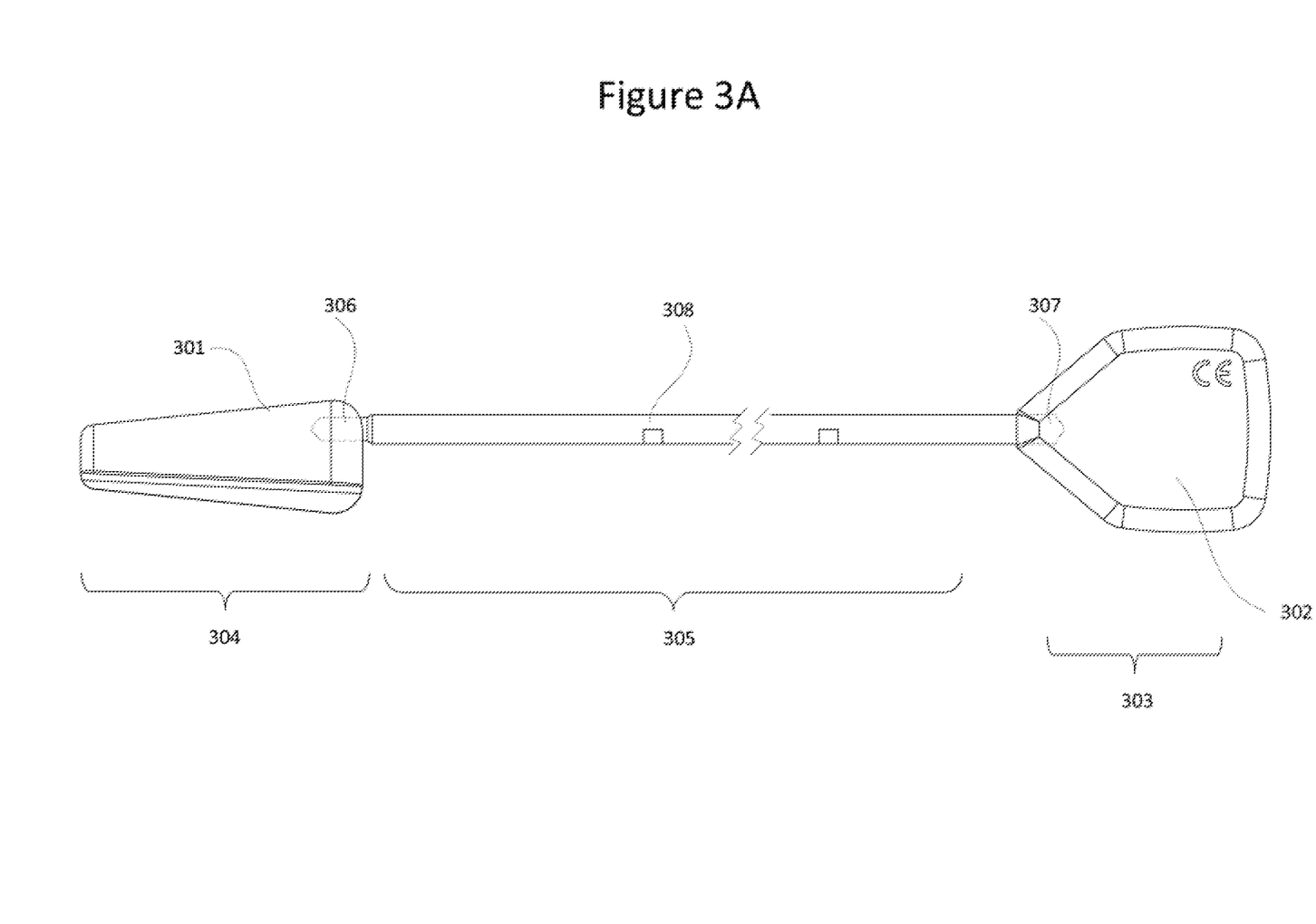
FIGS. 3A and 3B are cross-sectional views of the dilating head, stem and handle portions of the urethrotome according to embodiments of the invention.
Figure 3B:
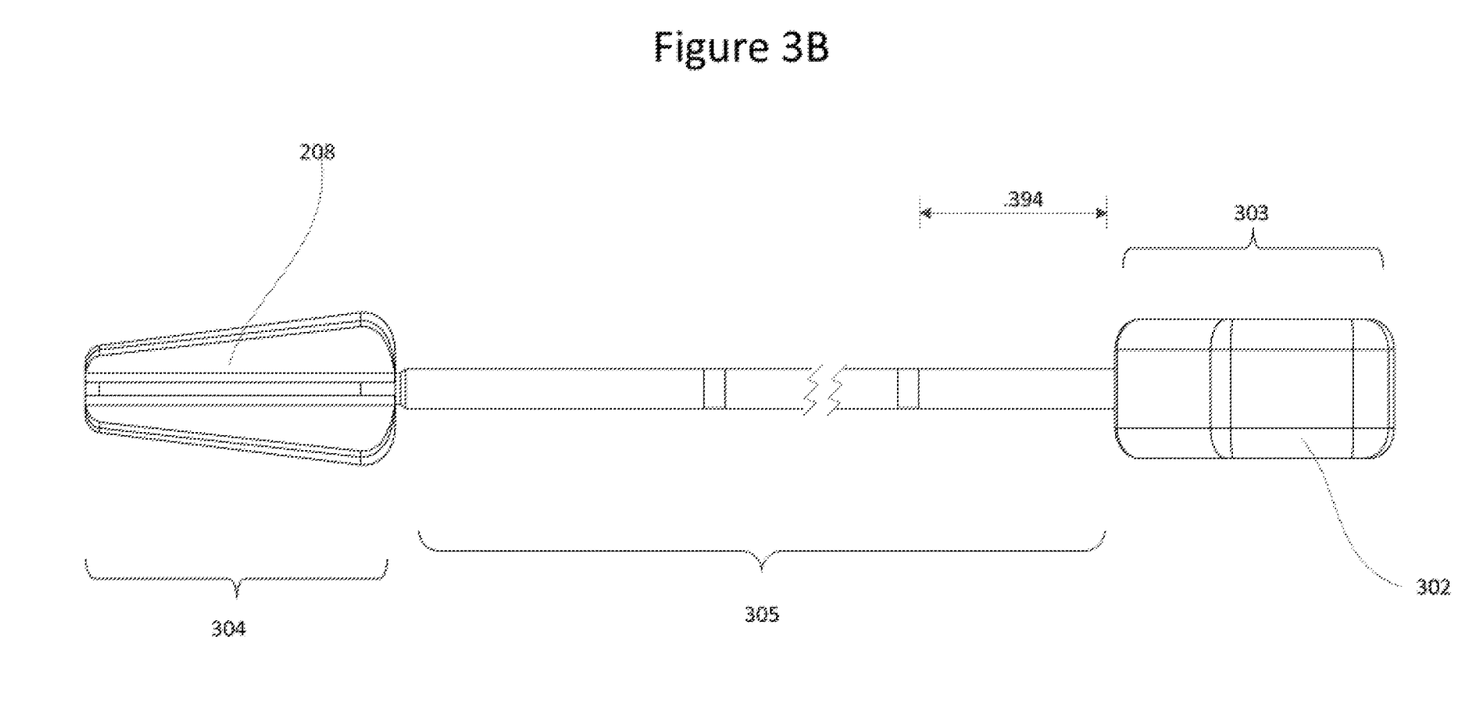

FIGS. 3A and 3B show a side view of the first distal end 301 coupled to a handle 302 at a second proximal end 303 via a stem 305. As FIG. 3A shows, one end of the stem 305 may be inserted into a recess 306 formed in the first distal end 301 of the dilator urethrotome, and a second end of the stem 305 may be inserted into a recess 307 formed in the handle 302. As described above, the dilating head may encounter friction or resistance in a stricture, which is transmitted through recess 306, stem 305, and recess 307 to handle 302 as tactile feedback. In some embodiments of the invention, the stem 305 may include markings or indents 308 that indicate a depth with which the dilating head has been inserted into the urethral stricture. In this way, the urethrotome indicates to the medical professional how deep the dilating should be located in a stricture.

In one aspect of the invention, handle 302 allows a medical professional to control the movement and maneuvering of the dilating head while it is in or advancing along the stricture. For example, the medical professional may control the sharp corners of the blade 208 of the dilating head to cut fibrous tissue by twisting or angling the handle. Likewise, the medical professional may control the blunt top edge of the blade 211 to push or move tissue by pushing, pulling, or angling the handle 302. As described above, the stem 305 is constructed from a flexible material such that if the control of the handle 302 causes pressure or tension to be applied at the stem 305, the stem 305 will flexibly bend allowing the medical professional to control the degree of pressure without causing undue discomfort or pain. Once the pressure or tension ceases, the material of the stem allows the stem 305 to return to its default position and shape. In some embodiments, the handle 302 may be substantially trapezoidal to allow the medical professional to maneuver the urethrotome by twisting, angling, or rotating the handle in all directions.

Figure 4:
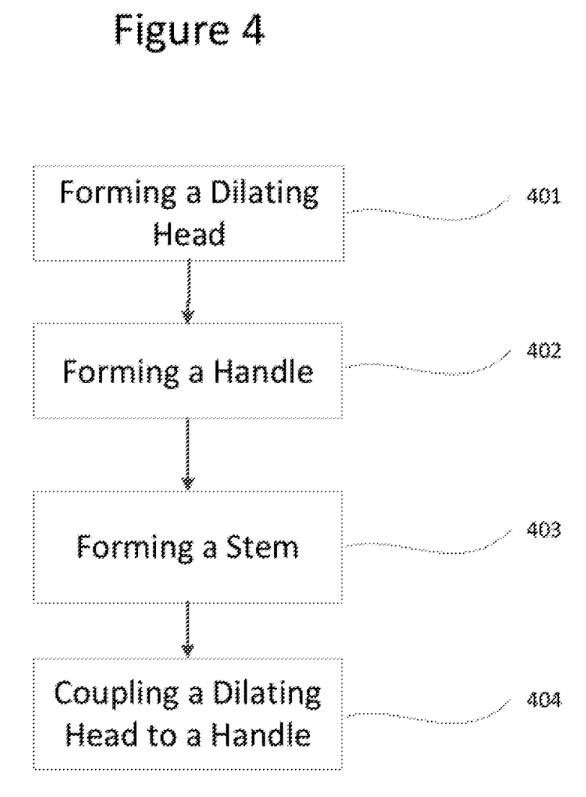
FIG. 4 is a method for forming a urethrotome dilator according to embodiments of the invention.

A method for providing a urethrotome dilator is shown in FIG. 4. The urethrotome dilator may be created by forming a dilating head, as shown in step 401, forming a handle, as shown in step 402, forming a stem, as shown in step 403, and coupling the dilating head to the handle via the stem, as shown in step 404.

The dilating head may be cast by creating a mold with a cavity in the shape and dimensions depicted in the cross-sectional views shown in FIGS. 2A and 2B. For example, the mold may have a cavity in the shape of a first region 201, second region 202, substantially conical surface 204 substantially flat surface 207, blade 208, top edge 211, and two opposing sides 212 and 213. Once the mold is formed, a filling may be inserted into the mold, where it may cool and solidify. Once solidified, the dilating head may be removed from the mold as a single solidified element. Thus, the first region, second region, and blade are integrally formed as one solid piece. The channel 203 and recess 214 may subsequently be formed by gun drilling or boring holes into the dilating head. The cast head may then be shaped with a computer-driven lathe and finished with electropolish.

In some embodiments of the invention, the material of the filling is made of surgical steel or biocompatible plastic, nitinol, and similar materials.

In steps 402 and 403, a handle and stem may be formed using the casting process described above. For example, a mold for casting a handle may be created with a cavity having a trapezoidal shape and the dimensions described above. Similarly, a mold for casting a stem may be created with a cavity having a cylindrical shape and the dimensions described above. The dilating head, stem, and handle may then be coupled by welding, soldering, or similar metal-joining techniques. Welding techniques may include laser welding.

Figure 5:
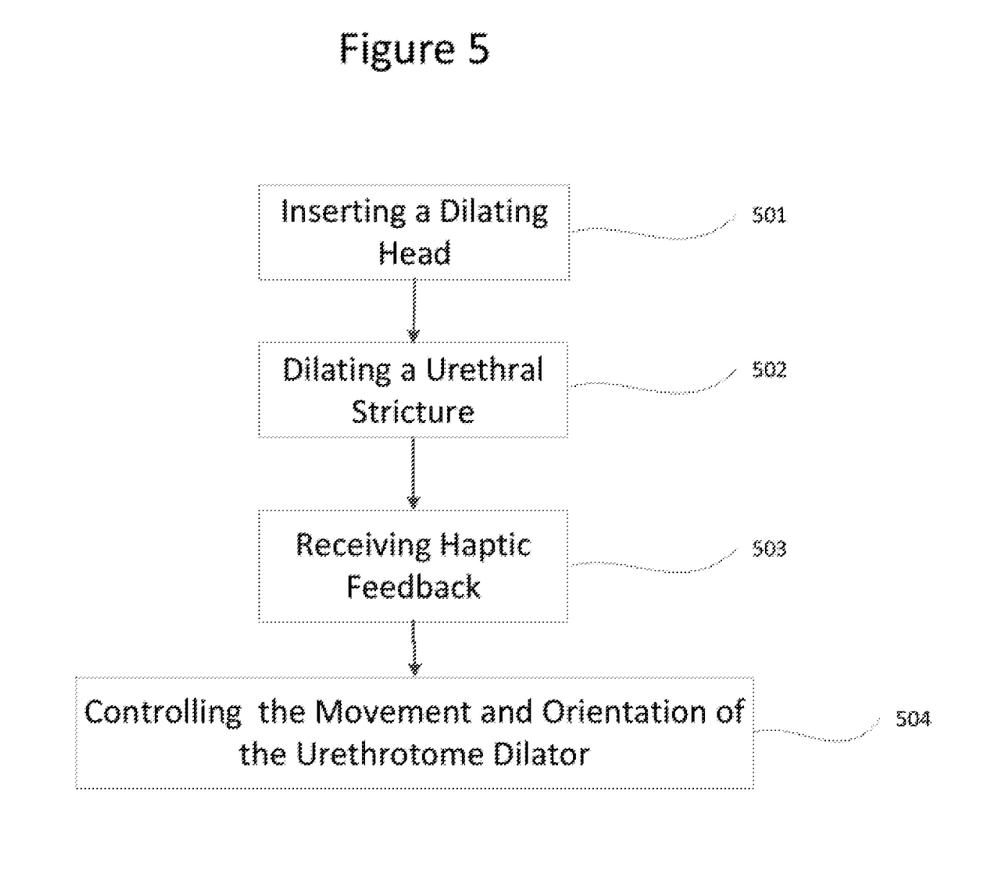
FIG. 5 is a method for advancing a urethrotome dilator through a urethral stricture according to embodiments of the invention.

A method for advancing a urethrotome dilator into a stricture is shown in FIG. 5. A medical professional may dilate a urethral stricture by inserting a dilating head into the stricture as shown in step 501, dilating the urethral stricture as shown in step 502, receiving feedback as shown in step 503, and controlling the movement and orientation of the urethrotome dilator based on the feedback as shown in step 504. For example, the feedback may indicate a presence of scar tissue; the medical professional may then control the movement and orientation of the handle to cut the scar tissue using the blade's sharp corners described above. Alternatively, the movement and orientation of the handle may be controlled to stretch the tissue using the blunt edge of the blade. As described above, the dilating head may have rounded tips or rears, which allow the urethrotome to gently move or stretch tissue both as it is being advanced to or through the stricture or removed from the stricture.

Further, as described above, the stem may be constructed of a material that allows it to flexibly bend and return to its original shape. For example, a medical professional may apply pressure to the stem to control the movement and orientation of the urethrotome dilator, which in turn causes the stem to bend. Once the medical professional removes the pressure applied to the stem, the stem will return to its position and shape immediately prior to receiving pressure.

In some embodiments of the invention, the step of inserting the urethrotome dilator may include the step of passing a guidewire through a urethreal stricture to a predetermined position, such as for example the bladder. Once the guidewire has been anchored, the guidewire may be passed through the channel of the dilating head. The medical professional may then control the position of the urethrotome dilator and advance it to the predetermined position, based on the position of the guidewire.

For example, a medical professional may initially pass a guide-wire into the urethra and through the stricture area into a patient's bladder. The urethrotome dilator is advanced over this guidewire until it reaches the area of stricture. As the top of the blade is dull it will not cut normal tissue, which slides away from the blade. As the dilator engages a narrowed area of stricture, the sharp edges of the blade engage and cut fibrous bands as the stricture is dilated by the conical configuration of the head. The fibrous bands which are under the stress of the dilation process are cut easily by the sharp corners of the blade. After the stricture is cut, a catheter is left indwelling for a short period of time to allow for the stricture to heal in an open position and prevent recurrence. Stricture recurrence is not always preventable.

Variations, modifications, and other implementations of what is described herein may occur to those of ordinary skill in the art without departing from the spirit and scope of the present invention and its claims. Various size configurations of the present invention may be passed through the urethra until the desired sized of the urethra is reached.

I claim:

1. A urethrotome dilator for dilating and cutting an urethral stricture, the urethrotome dilator comprising:
    a first distal end including a dilating head, the dilating head including:
        a first region having a round surface that tapers to a vertex at a distal end that forms a tip and a base at a proximal end of the dilating head,
        a second region having a flat surface and a blade for cutting and stretching tissue, the blade being integrally formed within the second region and extending from the flat surface, the blade having a distal blade end, a proximal blade end, a top edge, and two opposing sides, wherein the top edge of the blade is blunt, and the top edge of the blade and the two opposing sides of the blade form substantially sharp corners for cutting tissue, and the height of the blade is tapered from the proximal blade end to the distal blade end, and a channel formed longitudinally through the dilating head for receiving a guidewire;
    a second proximal end including a handle for controlling the movement and orientation of the first distal end; and
    a stem that couples the first distal end to the second proximal end,
    wherein the flat surface extends from the vertex to the base of the dilating head and abuts the blade so that the blade is configured to stretch and cut tissue,
    wherein the first region and second region have a proximal end that forms a rear of the dilating head, the rear having a curved edge for dilating the urethral stricture while removing the urethrotome,
    wherein the channel extends through the geometric center of the dilating head from the tip through the base, and
    wherein the dilating head further comprises a recess for affixing the dilating head to the stem, the recess formed in the first region below the geometric center of the channel.

2. The urethrotome dilator of claim 1, wherein the base of the proximal end of the dilating head has a radius of 0.098 in.

3. The urethrotome dilator of claim 1, wherein the stem is configured to transmit resistance produced at the dilating head to the handle as haptic feedback, the haptic feedback indicative of a level of resistance encountered by the dilating head.

4. The urethrotome dilator of claim 1, wherein the stem is constructed of flexible material and configured to bend in response to pressure applied at the handle and the urethral stricture.

5. The urethrotome dilator of claim 4, wherein the stem is further configured to return to its default shape and position after the pressure applied at the handle and the urethral stricture is released.

6. The urethrotome dilator of claim 1, wherein the stem is constructed of surgical steel, biocompatible plastic, nitinol, and similar materials.

7. The urethrotome dilator of claim 1, wherein the top edge of the blade is at least 0.02 in wide.

8. The urethrotome dilator of claim 7, wherein the top edge of the blade and the two opposing sides form a 90° angle.

9. The urethrotome dilator of claim 1, wherein the height of the distal blade end of the dilating head from the flat surface is 0.015 in. and the height of the proximal blade end of the dilating head from the flat surface is 0.048 in.

10. The urethrotome dilator of claim 1, wherein diameter of channel is 0.047 in.

11. The urethrotome dilator of claim 1, wherein the recess further comprises spiral grooves that fasten the stem to the dilating head.

12. The urethrotome dilator of claim 1, wherein the handle includes a recess for affixing the handle to the stem.

13. The urethrotome dilator of claim 1, wherein the handle is trapezoidal.

14. The urethrotome dilator of claim 1, wherein the round surface of the dilating head forms an angle with respect to the channel between 4° and 9°.

15. The urethrotome dilator of claim 1, wherein the tapered top edge of the blade forms an angle with respect to the channel between 2° and 7°.

16. The urethrotome dilator of claim 1, wherein the stem further comprises markings that indicate a depth with which the dilating head has been inserted into the urethral stricture.

17. The urethrotome dilator of claim 1, wherein the tip has a curved edge for entering and dilating the urethral stricture while advancing the urethrotome.

18. The urethrotome dilator of claim 17, wherein the tip has a radius of curvature of 0.03 in.

19. The urethrotome dilator of claim 1, wherein the rear has a radius of curvature of 0.06 in.

20. A method of providing a urethrotome dilator, the method comprising:
    forming a dilating head having a first region with a round surface that tapers to a vertex at a distal end that forms a tip and a base at a proximal end of the dilating head a second region with a flat surface and a blade for cutting and stretching tissue, and channel formed longitudinally through the center of the dilating head for receiving a guidewire, the blade being integrally formed within the second region and extending from the flat surface, the blade having a distal blade end, a proximal blade end, a top edge, and two opposing sides, wherein the top edge of the blade is blunt, and the top edge of the blade and the two opposing sides of the blade form sharp corners for cutting tissue, and the height of the blade is tapered from the proximal blade end to the distal blade end;

forming a handle for controlling movement and orientation of the dilating head;

forming a stem for connecting the handle to the dilating head and providing haptic feedback of resistance encountered by the dilating head; and coupling the dilating head to the handle, wherein the flat surface extends from the vertex to the base of the dilating head and abuts the blade so that the blade is configured to stretch and cut tissue, wherein the first region and second region have a proximal end that forms a rear of the dilating head, the rear having a curved edge for dilating an urethral stricture while removing the urethrotome, wherein the channel extends through the geometric center of the dilating head from the tip through the base, and wherein the dilating head further comprises a recess for affixing the dilating head to the stem, the recess formed in the first region below the geometric center of the channel.

21. The method of claim 20, further comprising electropolishing the dilating head, stem, and handle.

22. The method of claim 20, wherein the step of coupling comprises welding, fastening, or applying bonding adhesive to join the dilating head to the handle.

23. The method of claim 20, wherein the step of forming the dilating head comprises:

casting the dilating head with a mold, the mold having a cavity with a round surface that tapers distally to form the first region, a flat cavity to form the second region, and a cavity to form the blade; and drilling a hole through a center axis of the dilating head to form the channel for receiving the guidewire.

24. A method of dilating and cutting an urethral stricture with a urethrotome dilator, wherein the urethrotome dilator has a first distal end including a dilating head, a second proximal end including a handle for controlling movement and orientation of the urethrotome dilator, and a stem that couples the first distal end to the second proximal end the dilating head, wherein the dilating head of the first distal end forms a first region having a round surface that tapers to a vertex at a distal end that forms a tip and a base at a proximal end of the dilating head, a second region having a flat surface and a blade for stretching tissue, and a channel formed longitudinally through the center of the dilating head for receiving a guidewire, the blade being integrally formed within the second region and extending from the flat surface, the blade having a distal blade end, a proximal blade end, a top edge, and two opposing sides, wherein the top edge of the blade is blunt, and the top edge of the blade and the two opposing sides of the blade form sharp corners for cutting tissue, and the height of the blade is tapered from the proximal blade end to the distal blade end, wherein the steps comprise:

inserting the dilating head of the urethrotome dilator into the urethral stricture;

dilating the urethral stricture with the dilating head;

receiving haptic feedback in response to the step of insertion, the haptic feedback indicative of a level of resistance encountered by the dilating head; and controlling the movement and orientation of the urethrotome dilator based on the haptic feedback, wherein the flat surface extends from the vertex to the base of the dilating head and abuts the blade so that the blade is configured to stretch and cut tissue, wherein the first region and second region have a proximal end that forms a rear of the dilating head, the rear having a curved edge for dilating the urethral stricture while removing the urethrotome, wherein the channel extends through the geometric center of the dilating head from the tip through the base, and wherein the dilating head further comprises a recess for affixing the dilating head to the stem, the recess formed in the first region below the geometric center of the channel.

25. The method of claim 24, wherein the step of inserting the urethrotome dilator comprises:

passing a guidewire through the urethral stricture to a predetermined position;

passing the guidewire through the channel of the dilating head; and controlling the position of the urethrotome dilator based on the position of the guidewire.

26. The method of claim 24, wherein the haptic feedback indicates a presence of scar tissue, and the step of controlling the movement and orientation of the handle comprises cutting the scar tissue.

27. The method of claim 24, wherein the haptic feedback indicates the presence of tissue, and the step of controlling the movement and orientation of the urethrotome dilator comprises stretching the tissue.

28. The method of claim 24, further comprising:

applying pressure to the stem to control the movement and orientation of the urethrotome dilator;

bending the stem in response to the pressure applied to control the movement and orientation of the urethrotome dilator;

removing the pressure applied to the stem; and returning the stem to its position and shape immediately prior to receiving pressure.

29. The method of claim 24, further comprising:

removing the urethrotome dilator from the urethral stricture; and dilating the urethral stricture with the dilating head as the urethrotome dilator is being removed.

* * * * *